United States Patent [19]

Edwards et al.

[11] Patent Number: 5,728,144
[45] Date of Patent: *Mar. 17, 1998

[54] STEERABLE COAXIAL CABLE SYSTEMS FOR CARDIAC ABLATION

[75] Inventors: Stuart D. Edwards, Los Altos; Jerome Jackson, Sunnyvale; Thomas M. Morse, San Jose; Patrick M. Owens, Cupertino, all of Calif.

[73] Assignee: EP Technologies, Inc., San Jose, Calif.

[*] Notice: The term of this patent shall not extend beyond the expiration date of Pat. No. 5,281,217.

[21] Appl. No.: 625,925

[22] Filed: Apr. 1, 1996

Related U.S. Application Data

[60] Continuation of Ser. No. 332,950, Nov. 1, 1994, abandoned, which is a division of Ser. No. 163,371, Dec. 7, 1993, Pat. No. 5,370,678, which is a continuation of Ser. No. 868,112, Apr. 13, 1992, abandoned.

[51] Int. Cl.[6] .......................................... A61B 1/00
[52] U.S. Cl. .................. 607/101; 607/156; 606/41; 604/95
[58] Field of Search ............... 606/41, 42, 45–50; 607/100–102, 115, 116, 154, 156; 604/95, 282; 128/772

[56] References Cited

U.S. PATENT DOCUMENTS

| | | |
|---|---|---|
| 4,409,993 | 10/1983 | Furihata ............................. 607/156 |
| 4,494,539 | 1/1985 | Zenitani et al. .................... 606/34 |
| 4,643,186 | 2/1987 | Rosen et al. ...................... 607/156 |
| 5,108,368 | 4/1992 | Hammerslag et al. ............. 604/95 |
| 5,195,968 | 3/1993 | Lundquist et al. ................. 604/95 |
| 5,273,535 | 12/1993 | Edwards et al. .................... 604/95 |
| 5,281,217 | 1/1994 | Edwards et al. .................... 606/41 |

*Primary Examiner*—Michael Peffley
*Attorney, Agent, or Firm*—Ryan, Maki, Mann & Hohenfeldt

[57] ABSTRACT

A coaxial cable assembly has an associated steering mechanism for maneuvering the assembly within the body.

33 Claims, 8 Drawing Sheets

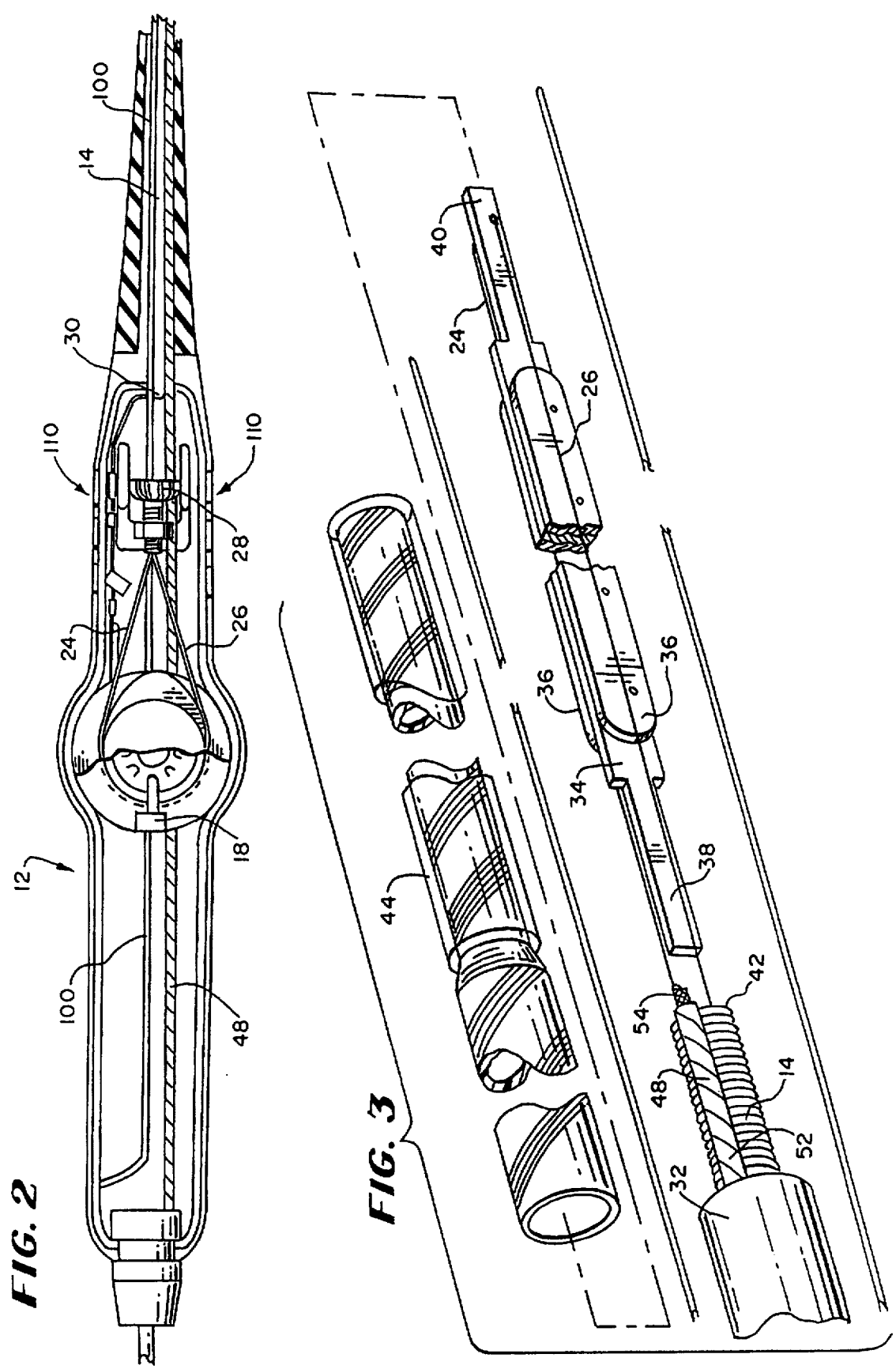

FIG. 4
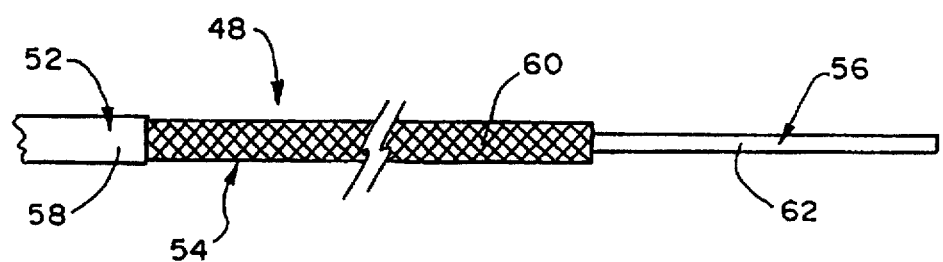
FIG. 5 A
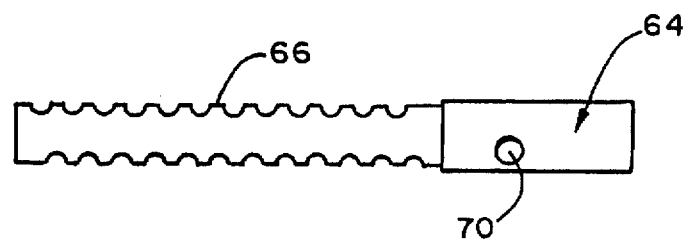
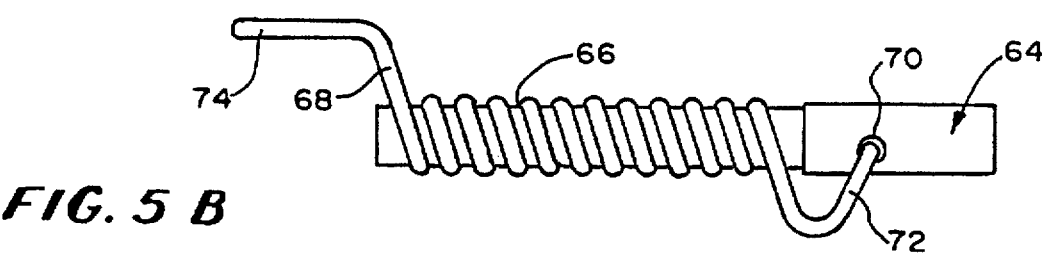
FIG. 5 B

FIG. 6A
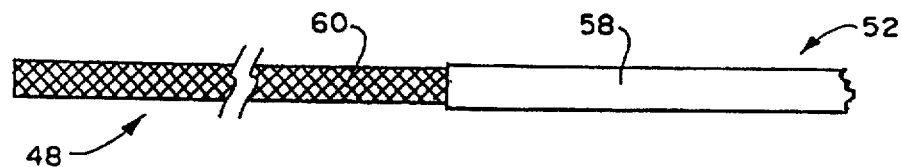
FIG. 6B
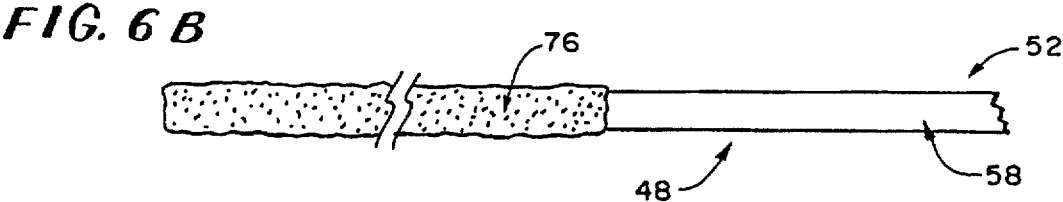
FIG. 6C
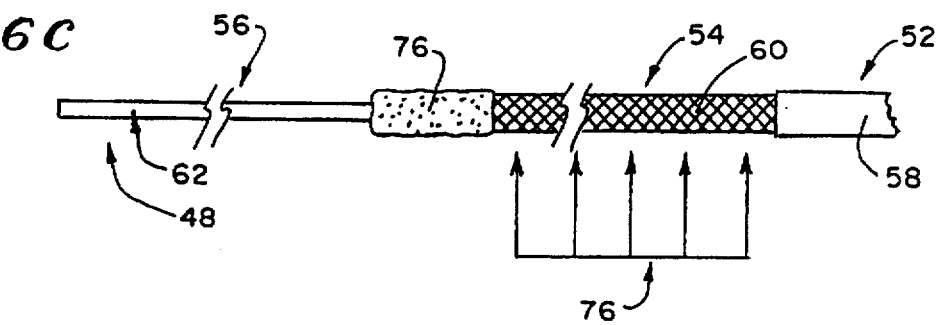
FIG. 7A
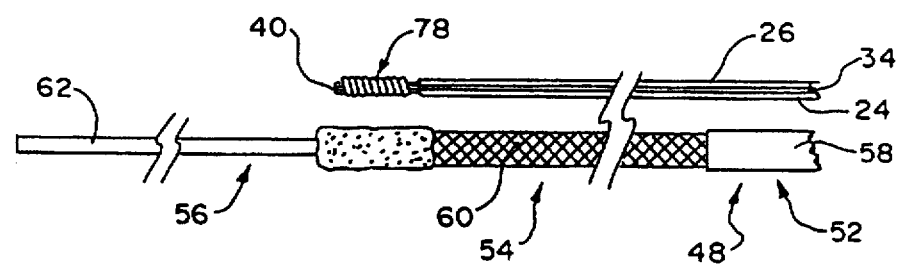
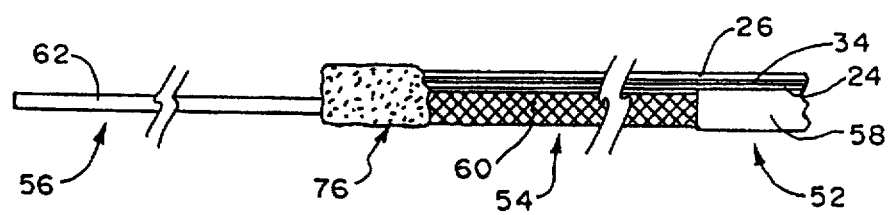
FIG. 7B

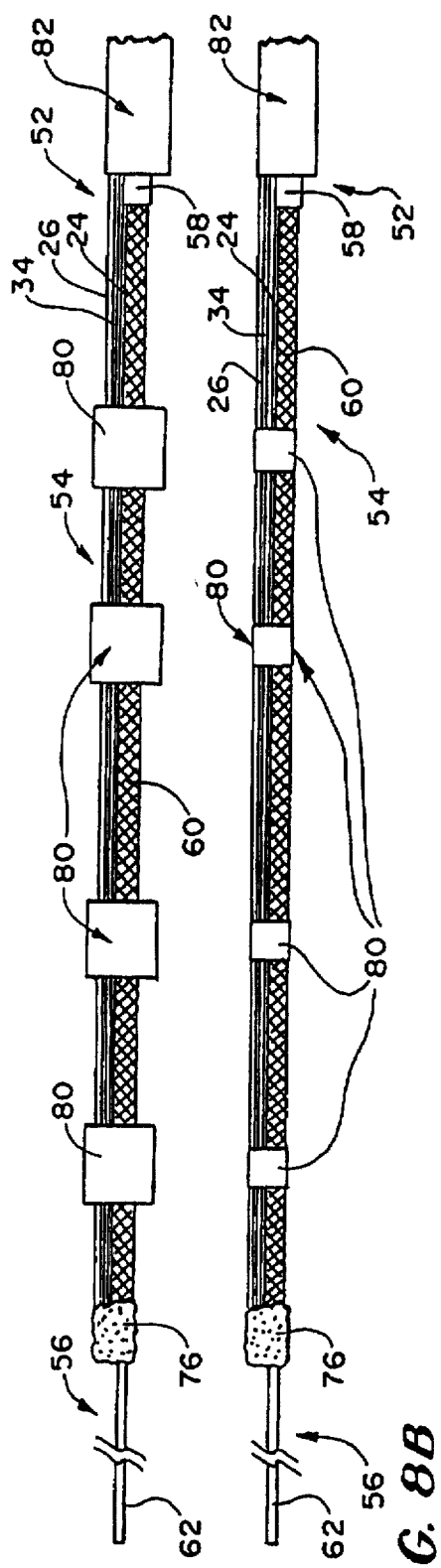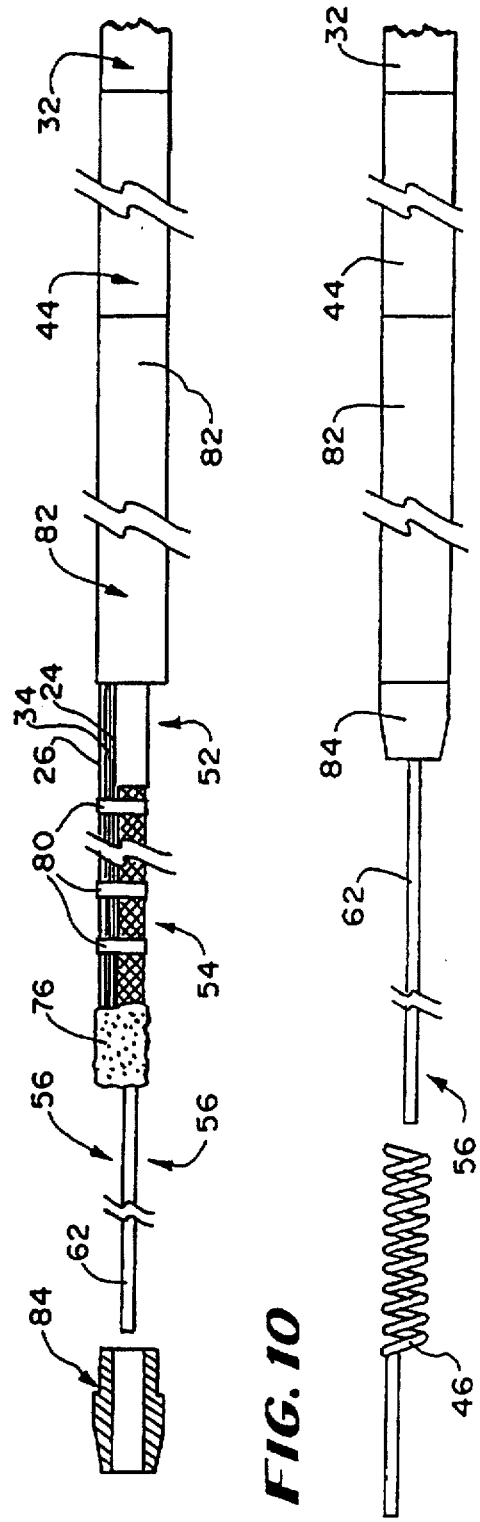

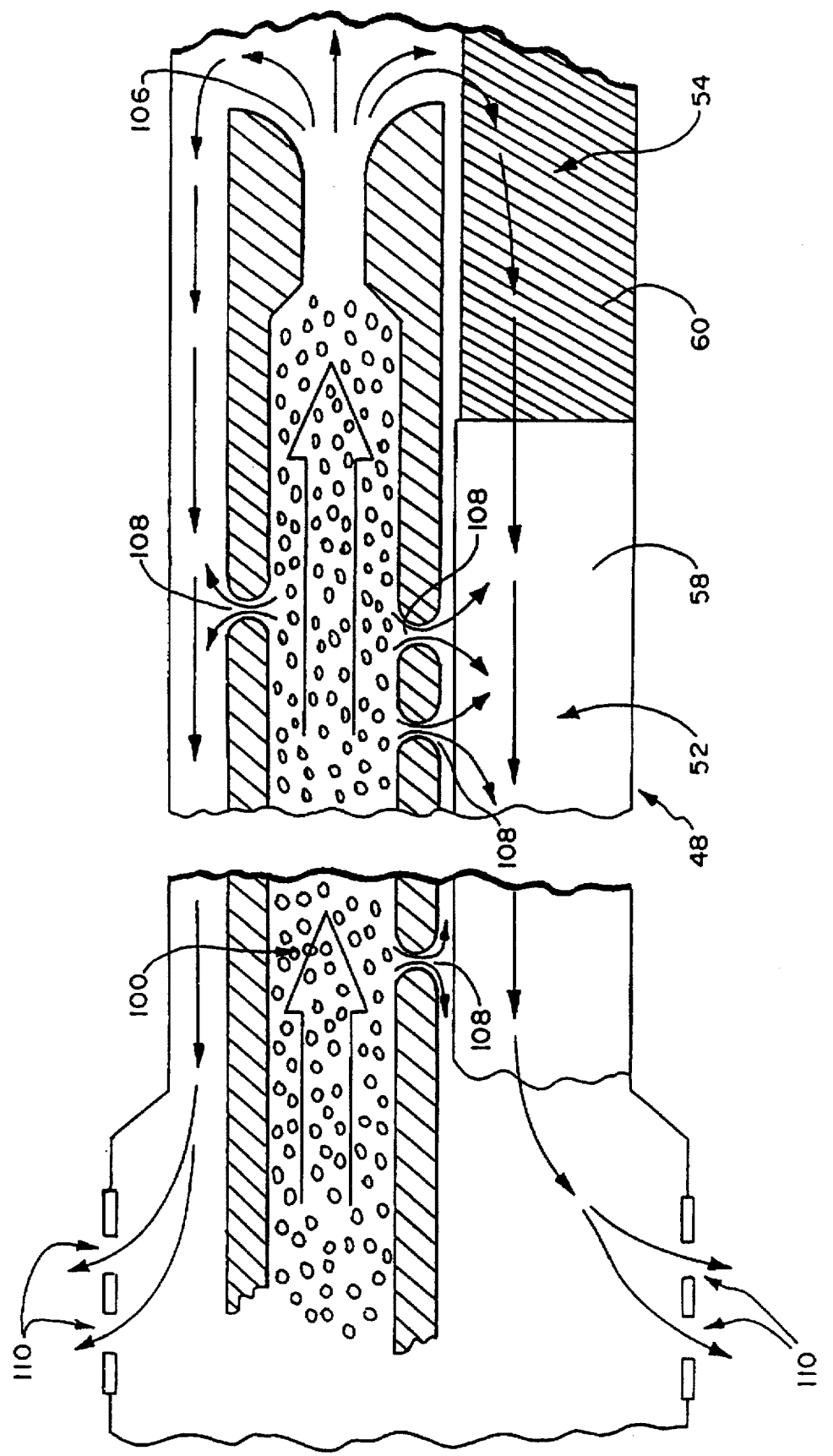

STEERABLE COAXIAL CABLE SYSTEMS FOR CARDIAC ABLATION

This is a continuation of application Ser. No. 08/332,950 filed on Nov. 1, 1994 abandoned which is a divisional of application Ser. No. 08/163,371 filed on Dec. 7, 1993, now U.S. Pat. No. 5,370,678, which is a continuation of application Ser. No. 07/868,112 filed on Apr. 13, 1992 (abandoned).

FIELD OF THE INVENTION

The invention generally relates to cardiac ablation catheters and systems. In a more specific sense, the invention relates to catheters that use microwave energy to ablate ventricular and atrial tachycardia foci for the treatment and control of cardiac arrhythmias.

BACKGROUND OF THE INVENTION

Physicians make use of catheters today in medical procedures to gain access into interior regions of the body to ablate tissue areas. It is important for the physician to be able to accurately steer the catheter to the ablation site. Once at the site, it is important for the physician to control the emission of energy within the body used to ablate the tissue.

The need for accurate steering and precise control over the catheter is especially critical during procedures that ablate tissue within the heart. These procedures, called electrophysiology therapy, are becoming increasingly more widespread for treating cardiac rhythm disturbances, called arrhythmias.

During these procedures, a physician steers a catheter through a main vein or artery (which is typically the femoral artery) into the interior region of the heart that is to be treated. The physician then further manipulates a steering mechanism to place the electrode carried on the distal tip of the catheter into direct contact with the tissue that is to be ablated. The physician directs radio frequency (RF) energy from the electrode tip through the tissue to an indifferent electrode to ablate the tissue and form a lesion.

Some clinicians have suggested the use of microwave energy for cardiac ablation. For example, Langberg U.S. Pat. No. 4,945,915 proposes the use of a helical microwave antenna fed by a coaxial line to thermally ablate cardiac tissue. The radiation heating patterns that microwave energy propagate can, in theory at least, form lesions that are deeper than the lesions formed by the conductive heating patterns generated by conventional RF energy.

The ability of microwave energy to form deeper lesions also raises challenges in antenna system design. To gain all the benefits of using microwave energy, the clinician must be able to control the type and the distribution of heating patterns propagated at the intended lesion site. If a microwave antenna system also propagates unintended conductive heating patterns, the temperature of the ablation site can be quickly elevated above a critical isotherm (thought to be in the range of 53 to 55 degrees C.) before the desired lesion depth is achieved. Irreversible tissue damage can result. The same unintended conductive heating patterns can also quickly heat the blood pool around the ablation site, causing undesired coagulation.

Ablation systems and processes using microwave energy will not find widespread clinical use, if they cannot be made and controlled to minimize the propagation of conductive heating patterns. They will also fail to find widespread use, if the microwave antenna cannot be conveniently steered and positioned to the desired ablation site within the heart.

SUMMARY OF THE INVENTION

The inventions provide improved cardiac ablation systems and methods using coaxial cables with energy transmitting elements. The improved systems and methods offer a coaxial cable assembly for cardiac ablation catheters that is associated with a steering mechanism for maneuvering the assembly within the body. In a preferred embodiment, the coaxial cable has a proximal region for connection to a source of energy and a distal region for propagating the energy. The coaxial cable also has an intermediate region between the distal and proximal regions that has a greater degree of flexibility than the proximal region.

The steering mechanism is connected directly to the intermediate region of the coaxial cable. The mechanism extends from there to an actuator located at the proximal region of the coaxial cable. The actuator is operative by the user to bend the intermediate region and, with it, the distal energy propagation region of the coaxial cable.

BRIEF DESCRIPTION OF THE DRAWINGS

FIG. 2 is a top section view, taken along line 2—2 in FIG. 1, of the interior of the handle associated with the catheter;

FIG. 3 is an exploded enlarged perspective view of the steering mechanism associated with the catheter;

FIG. 4 is a view of the three functional regions of the coaxial cable associated with the catheter;

FIGS. 5 to 13 show the steps involved in making the catheter shown in FIG. 1;

FIG. 16 is an enlarged view of the heat absorbing mechanism shown in FIG. 15.

DESCRIPTION OF THE PREFERRED EMBODIMENTS

Figure 1:
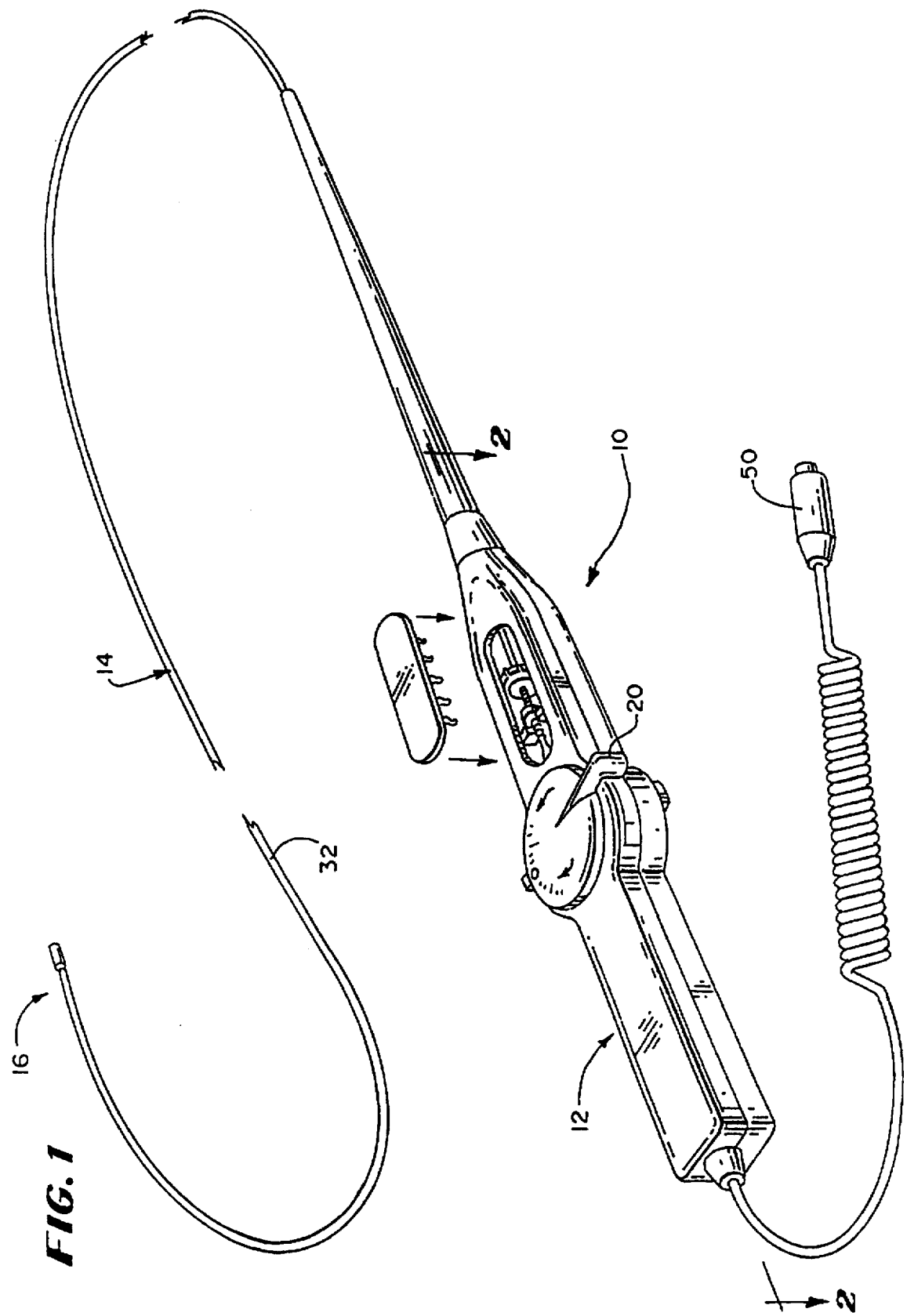
FIG. 1 is a perspective view of a catheter having a steerable coaxial antenna assembly that embodies the features of the invention.
Figure 11:
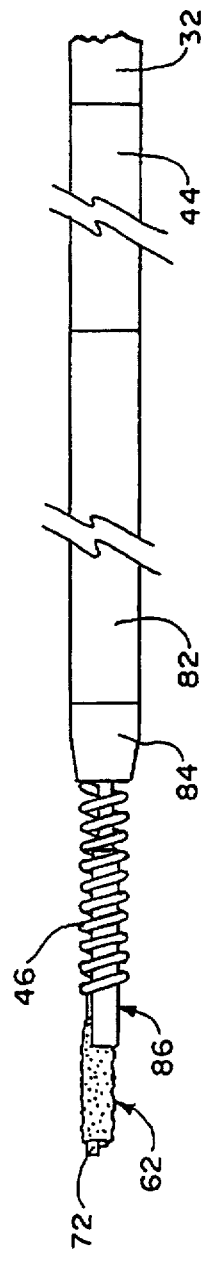

FIG. 1 shows a steerable microwave ablation catheter 10 that embodies the features of the invention. The catheter 10 includes four main parts: a handle 12, a guide tube 14, and a steerable coaxial antenna assembly 16. In use, the catheter 10 provides electrophysiology therapy in the interior regions of the heart.

When used for this purpose, a physician grips the handle 12 and maneuvers the guide tube 14 through a main vein or artery (which is typically the femoral arterial) into the interior region of the heart that is to be treated. The physician then further steers the coaxial antenna assembly 16 to place it in contact with the tissue that is to be ablated. The physician directs energy to the antenna assembly 16 to ablate the tissue contacted.

As FIG. 2 shows, the handle 12 encloses a rotating cam wheel 22, which forms a portion of the steering mechanism for the antenna assembly 16. An associated external steering lever 20 (see FIG. 1) rotates the cam wheel 22 to the left and to the right.

The cam wheel 22 carries a wire fastener 18. The wire fastener 18 holds the proximal ends of right and left catheter steering wires 24 and 26, which are soldered or glued to the interior of the fastener 18.

As FIG. 2 shows, the steering wires 24 and 26 extend from the opposite ends of the fastener 18 and along the associated left and right side surfaces of the cam wheel 22. The steering wires 24 and 26 extend through interior bore of a tension screw 28 and into the proximal end 30 of the guide tube 14.

The guide tube 14 is a flexible shaft attached to the handle 12. While it can be variously constructed, in the illustrated embodiment, the guide tube 14 is a length of stainless steel coiled into a flexible spring enclosing an interior bore. A braided sheath 32 of plastic material encloses the guide tube 14. The steering wires 24 and 26 pass through the interior bore, which leads to the antenna assembly 16.

As FIG. 3 shows, the steering mechanism for the antenna assembly 16 also includes a bendable main support wire 34. In the illustrated embodiment, the main support wire 34 is made of stainless steel flat wire stock in an elongated shape about 0.035 inch wide and about 0.005 inch thick. The main support wire 34 is about 3 inches in total length.

Preferably, two leaf springs 36 sandwich the main support wire 34, stiffening it. Each leaf spring 36 is made of stainless steel flat wire stock in an elongated shape that is about 0.039 inch wide and about 0.0029 inch thick.

The opposite ends of the main support wire 34 are cut away to form stepped shoulders 38 and 40. In the illustrated embodiment, the shoulders 38 and 40 are about 0.024 inch wide and aligned along the centerline of the main support wire 34. Each shoulder 38 and 40 is about 0.12 inch in length.

As FIG. 3 shows, one stepped shoulder 38 is attached to the distal end 42 of the guide tube 14. A sleeve assembly 44 encloses and reinforces the junction of the guide tube end 42 and the main support wire 34. The sleeve assembly 44 terminates well short of the stepped shoulder 40, leaving it exposed for attachment of the distal ends of the right and left steering wires 24 and 26. As FIG. 3 diagrammatically shows, the left and right steering wires 24 and 26 are ultimately attached, respectively, to the right and left sides of the stepped shoulder 40.

The antenna assembly 16 includes an antenna 46 (see FIG. 13) and an associated coaxial cable 48. The proximal end of the cable 48 extends from within the handle 12 (as FIG. 2 shows), along the outside of the guide tube 14 within the sheath 32. A plug 50 joined to the proximal end of the cable 48 extends outside the handle 12. The plug 50 connects the cable 48 to a source of energy. The cable 46 conducts this energy to the antenna 46 for propagation at the lesion site.

According to one aspect of the invention, the coaxial cable 48 includes three, functionally different regions 52, 54, and 56.

The first region 52 constitutes the majority of the coaxial cable 48. It is enclosed within an outer insulation sheath 58 and runs along the outside of the guide tube 14, as previously described. In a preferred embodiment, the sheath 58 has an outer diameter of about 0.06 inch.

The second region 54 begins near the junction of the main support wire 34 with the guide tube 14. In the second region 54, the outer sheath 58 is absent, leaving a metallic mesh shield 60 that surrounds the core cable wire 62. In an preferred embodiment, the mesh shield 60 has an outer diameter of about 0.054 inch. With the removal of the relatively bulky outer sheath 58, the second region 54 is significantly more flexible than the first region 52. In a preferred embodiment, the second region 54 extends for about 3 inches.

The steering mechanism for the antenna assembly 16 is ultimately attached to the flexible second region 54 of the coaxial cable 48.

The third region 56 occupies the distal end of the cable 48. Here, there is no surrounding sheath or shield, leaving the core conductor 62 of the cable 48 exposed. In a preferred embodiment, the core conductor 62 is silver coated copper having an outer diameter of about 0.018 inch and a length of about 0.75 inch. The third region 56 ultimately functions as or as part of the antenna 46.

FIGS. 5 to 13 show the steps in a preferred method of assembling the steerable coaxial antenna assembly 16 just generally described.

In the first step (FIGS. 5A and 5B), the practitioner shapes the antenna 46. In the illustrated embodiment, the antenna 46 is helical is shape, but other shapes can be selected.

In this arrangement, the practitioner uses a wire coiling mandrel 64 to form the helical shape. The mandrel 64 includes a threaded end 66. The threaded end 66 has the radius and pitch required to create an antenna that will propagate the desired radiation heating patterns at the operating frequency selected.

In the illustrated embodiment, the threaded mandrel end 66 forms a helical configuration having an internal diameter of about 0.56 inch; an outer diameter of about 0.104 inch; and a pitch of about 24 turns to the inch.

The practitioner passes a length of antenna wire 68 through an opening 70 to secure it to the mandrel 64. Various types of antenna wire can be used. In the illustrated embodiment, 5% silver coated copper wire having an outer diameter of about 0.023 inch is used. The practitioner winds the wire 68 tightly about the threaded mandrel end 66, forming it into the helix shape.

Once formed, the practitioner unscrews the helix antenna 46 from the mandrel. The practitioner cuts the antenna 46 to the desired length. In the illustrated embodiment, the desired length is 10 turns. The operating frequencies of the antenna so made is either about 915 MHz or 2450 Mhz.

When so formed, the antenna 46 has a forward end 72 and a rearward end 74. Before proceeding further, the practitioner preferably uses a deburring tool to remove the silver on the rearward antenna end 74. This deburring exposes the inner copper core of the antenna 46.

In the next step (see FIGS. 6A, 6B, and 6C), the practitioner forms the three regions 52, 54, and 56 in the cable 48. The practitioner first strips away 1.1 inch of the outer shield 58 from the end of the cable 48. This exposes the metallic mesh shield 60 (as FIG. 6A shows).

This exposed shield 60 is next tinned with solder (as FIG. 6B shows). Various solder coatings can be used. In the illustrated embodiment, a 95% tin/5% silver solder mix is used. The practitioner preferably cuts off about 0.002 inch of the tin coated shield 60 to expose the copper core of the cable 48 before proceeding to the next step.

The practitioner then removes about 0.75 inch of the tin coated shield 60 to expose the core conductor 62 (as FIG. 6C shows). This exposed area becomes the third region 56 of the cable 48.

The practitioner than removes an additional amount of the sheath 58 beyond the already tinned shield 60 to expose a total of about 3 inches of the metallic mesh shield 60, of which about 0.175 inch remains tin coated. This forms the second region 54 of the cable 48. The remaining portion of the cable 48 (still enclosed within the sheath 58) becomes the first region 52 of the cable 48.

As FIG. 6C also shows, the practitioner preferably applies an electroplastic conforming coating 76 to the second cable region 54 that is not tin coated. The conforming coating 76 imparts greater strength to the flexible second region 54. It compensates for the absence of the sheath 58, but does not reduce the degree of flexibility required.

Various conforming coatings 76 can be used. The illustrated embodiment uses an electroplastic silicone coating sold by Chemtronics under the tradename Konoform.

In the next step (shown in FIGS. 7A and 7B), the practitioner solders the steering mechanism to the solder coated distal end of the flexible, second cable region 54. First, the practitioner solders the steering wires 24 and 26 to the right and left sides of the support wire shoulder 40.

As FIG. 7A shows, the practitioner preferably wraps and solders small gauge tin signal wire 78 around the junction of the steering wires 24 and 26 to the stepped shoulder 40. The wire wrap 78 imparts greater strength to this critical area of the steering mechanism. The wire wrap 78 holds the steering wires intimately against the stepped shoulder 40 both during and after their connection to the tinned end of the flexible, second cable region 54 (as FIG. 7B shows).

Next (as FIGS. 8A and 8B show), the practitioner preferably shrink fits a series of plastic rings 80 (for example, made of polyolefin material) about the main support wire 34, steering wires 24 and 26, and the underlying flexible second cable region 54. FIG. 8A shows the rings 80 before heat shrinking; FIG. 8B shows the rings 80 after heat shrinking.

The rings 80 hold the steering wires 24 and 26 and the main support wire 34 snugly against the flexible second cable region 54. In this step, the practitioner also preliminarily slides an outer protective distal sleeve 82 over the coaxial cable and the now integrally attached steering mechanism.

In the next step (see FIG. 9), the practitioner affixes an end cap 84 about the stripped and solder coated second cable region 54, to which the steering mechanism is now integrally joined. The end cap 84 is attached using a suitable adhesive, like locktite. The third cable region 56 (i.e., the exposed core conductor 62) extends through the attached cap 84.

As FIG. 10 shows, the practitioner now slides the previously formed helical antenna 46 into position over the exposed core conductor 62.

Next (see FIG. 11), the practitioner positions a temporary centering tool 86 between the core conductor 62 and the antenna 46. The centering tool 86 aligns the helical antenna centrally about the core conductor 62. The practitioner now solders the forward antenna end 72 to the core conductor 62. The practitioner removes the temporary centering tool 86 after making the soldered connection.

Figure 12:
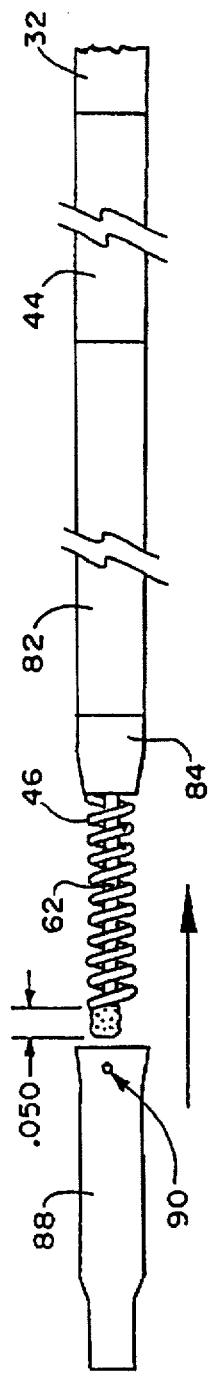

After trimming away the excess wire at the soldered connection, it is preferably shaped to a blunt, tapered point, exposing the copper core (as FIG. 12 shows).

Next (as FIG. 12 shows), the practitioner surrounds the assembly of the core conductor 62 and helical antenna 46 with a mold tube 88. The mold tube 88 is made of a flexible plastic material (for example, Teflon). One end fits snugly about the end cap 84. A small air vent hole 94 is drilled in this end next to the cap 84. The other end extends from the cap 84 and tapers to an opening 90 having a reduced diameter.

The practitioner next injects a potting compound 92 into the fitted mold tube 88 through the tapered opening 90. The potting compound 92 fills the tube 88, completely encompassing the assembly of the core conductor 62 and helical antenna 46. The practitioner stops the injection when the compound 92 begins to leak from the air vent hole 94.

According to another aspect of the invention, the potting compound 92 includes a material that has the combined characteristics of (i) a high dielectric constant; (ii) low microwave energy loss; and (iii) high thermal conductivity.

In the illustrated embodiment, a material like diamond or sapphire is used to impart these characteristics. In the illustrated embodiment, the compound 92 is made by adding one unit part of diamond dust (about 1 micron) to one unit part of a medical grade epoxy mix. The one unit part of the epoxy mix consists of ½ resin and ½ hardener.

The practitioner allows the injected potting compound 92 to air cure for about 5 minutes. Then, the practitioner places the potted assembly into an oven, where it cures for 30 minutes at 150 degrees F.

Figure 13:
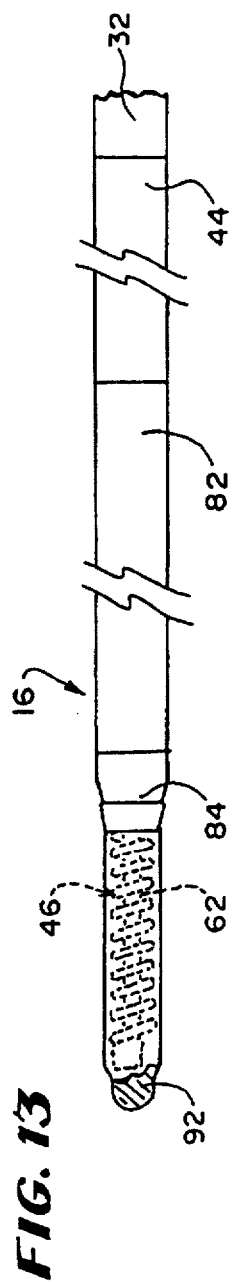

After curing, the practitioner removes the mold tube 88 (see FIG. 13). The end of the cured potted compound 92 is shaped to a blunt tip. The distal sleeve 82 is slid into place and attached to the cap 84 by an adhesive.

When so assembled, rotation of the cam wheel 22 in the handle 12 laterally pulls on the steering wires 24 and 26 attached to the flexible second region 54 of the cable 48. By rotating the cam wheel 22 to the left, the second cable region 54, and with it, the antenna 46 itself, bends to the left. Likewise, by rotating the cam wheel 22 to the right, the second cable region 54, and with it the antenna 46 too, bends to the right. The absence of the sheath 58 in the second region 54 imparts flexibility to the coaxial cable 48, making it an integral part of the steering mechanism for the antenna 46.

Furthermore, the potting compound 92 that encapsulates the entire assembly of the core conductor 62 and antenna 46 provides at least three benefits. First, the compound 92 provides a high dielectric constant for the antenna 46. Second, by minimizing the loss of microwave energy by the antenna 46, the compound 92 maximizes the propagation of the desired radiation heating patterns about the antenna 46. Third, the compound 92 has high thermal conductivity that dissipates any undesirable conductive heat patterns about the antenna 46.

Figure 14:
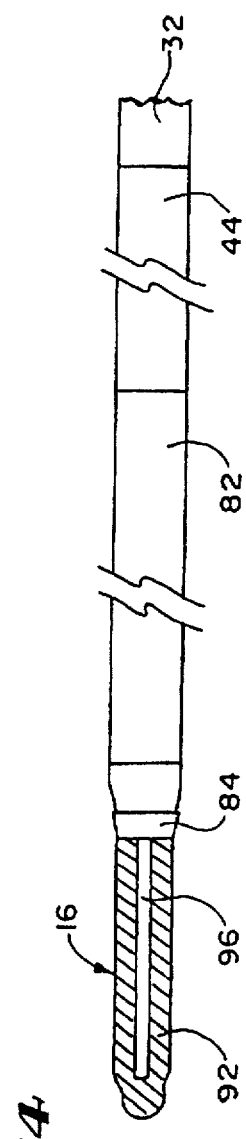
FIG. 14 is an alternative embodiment of a steerable coaxial antenna assembly that embodies the features of the invention.

FIG. 14 shows a whip microwave antenna assembly 96 that has been encapsulated by the potting compound 92 that embodies the features of the invention. The method of making the assembly 96 shown in FIG. 14 generally follows the same progression of steps as previously described, except that in FIG. 14, the core conductor 62 itself serves as the antenna. Other microwave antenna structures can be similarly encapsulated within the potting compound and attached to a steering mechanism to achieve the benefits of the invention.

Figure 15B:
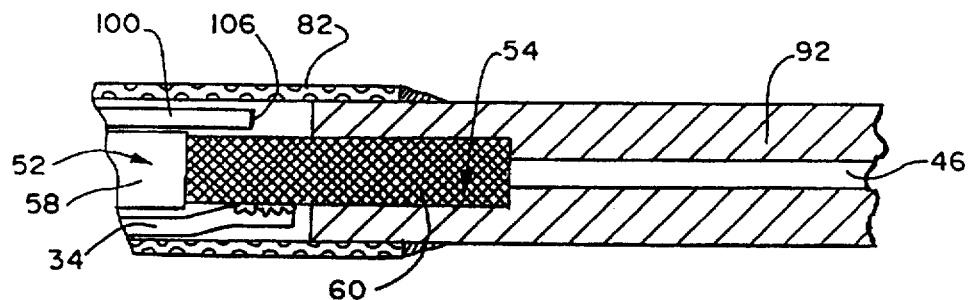
FIG. 15 is a coaxial antenna assembly that includes a mechanism for absorbing heat along the coaxial cable that embodies the features of the invention.
Figure 15A:
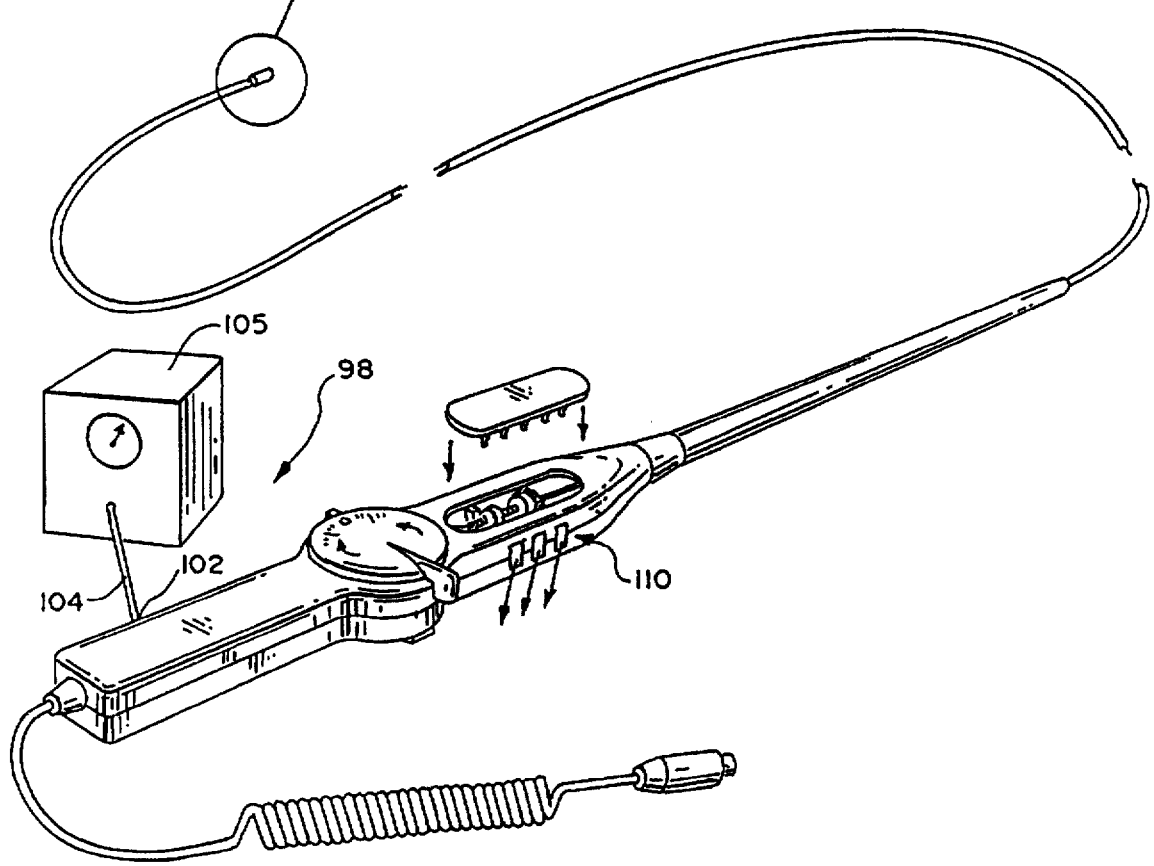

FIGS. 15 and 16 show another aspect of the invention that serves to reduce the propagation of conductive heating patterns by the antenna 46 and the attached coaxial cable 48. According to this aspect of the invention, the catheter 10 carries an assembly 98 for cooling the coaxial cable 48 and antenna 46 during use.

The cooling assembly 98 includes flexible tubing 100 that extends alongside the first and second regions 52 and 54 of the coaxial cable 48. The proximal end 102 of the tubing 100 is located within the catheter handle 12. An external supply tube 104 extends from the handle 12 and connects this end 102 of the tubing 100 to an external source 105 of pressurized gas, like carbon dioxide. The distal end 106 of the tubing 100 terminates in the second cable region 54, where the potting compound 92 encasing the antenna 46 begins.

The tubing 100 includes one or more expansion orifices 108. In the illustrated embodiment, the orifices 108 are formed at spaced intervals along the length of the tubing 100 and at its distal end 106.

In use, the pressurized gas conveyed by the tubing 100 exits the orifices 108 and expands. The expanding gas absorbs conductive heat propagated by the antenna 46 and the coaxial cable 48. The gas travels back along the guide tube 14 and vents out through openings 110 in the catheter handle 12.

The inventions provide a steerable ablation catheter that delivers energy to the ablation site using an coaxial cable. The steering mechanism the inventions provide make possible the fabrication of highly steerable microwave antenna systems for cardiac ablation purposes.

The inventions also provide a microwave antenna assembly for an ablation catheter that maximizes the propagation of radiation heating patterns for deep lesion formation while minimizing the propagation of conductive heating patterns that cause tissue damage and blood coagulation.

Various features and benefits of the inventions are set forth in the following claims.

We claim:

1. A steerable coaxial antenna assembly for a catheter comprising a coaxial cable having a proximal region for connection to a source of energy and a distal region connected to an antenna carried on said distal region for propagating energy, the coaxial cable having an intermediate region between the distal and proximal regions that has a greater degree of flexibility than the proximal region, and a support wire connected directly to the intermediate region of the coaxial cable to bend the intermediate cable region in response to bending force applied to the support wire, a steering wire attached to the support wire and extending from there to a mechanism located at the proximal region of the coaxial cable, the mechanism being operative by the user to apply bending force to the support wire to bend the intermediate region and, with it, the distal region of the coaxial cable relative to its proximal region.

2. An assembly according to claim 1 and further including a guide tube having a distal region joined to the support wire for positioning the support wire and for holding the support wire while it bends in response to external forces, and wherein the steering wire extends through the guide tube for attachment to the support wire to apply bending force.

3. An assembly according to claim 2 wherein the coaxial extends along the exterior of the guide tube.

4. An assembly according to claim 1 and further including solder joining the support wire directly to the intermediate region of the coaxial cable.

5. An assembly according to claim 1 and further including material wrapped about the center support wire and the intermediate cable region joining the support wire directly to the intermediate region of the coaxial cable.

6. An assembly according to claim 5 wherein the material includes shrink fit tubing.

7. An assembly according to claim 1 and further including material wrapped around the steering wire to hold the steering wire against the support wire.

8. An assembly according to claim 1 wherein the intermediate region includes an electroplastic conforming coating.

9. A catheter comprising a guide tube having a distal end, a center support wire that is bendable in response to external forces and having a proximal end that is joined to the guide tube for holding the center support wire while it bends in response to external forces, a steering wire attached to the distal end of the center support wire for applying a bending force, a coaxial cable having a first region that extends along the guide tube, a second region that extends beyond the guide tube, and a intermediate region that extends beyond the second region and includes antenna means for propagating energy, the second cable region having a greater degree of flexibility than the first cable region, and means connecting the distal end of the center support directly to the second cable region for bending the second cable region in response to the bending force applied by the steering wire to the center support wire.

10. An assembly according to claim 9 wherein the means for joining the center support wire directly to the second cable region includes means wrapped around the center support wire and the intermediate cable region.

11. An assembly according to claim 10 wherein the wrapped means includes shrink fit tubing.

12. An assembly according to claim 9 wherein the attachment between the steering wire and the center support wire includes means wrapped around the steering wire to hold the steering wire against the center support wire.

13. An assembly according to claim 9 wherein the intermediate cable region includes an electroplastic conforming coating.

14. A steerable microwave antenna assembly for a catheter comprising a microwave antenna, a coaxial cable having a proximal region for connection to a source of energy and a distal region connected to the microwave antenna for propagating energy, the coaxial cable having an intermediate region between the distal and proximal regions that has a greater degree of flexibility than the proximal region, and a support wire connected directly to the intermediate region of the coaxial cable to bend the intermediate cable region in response to bending force applied to the support wire, a steering wire attached to the support wire and extending from there to a mechanism located at the proximal region of the coaxial cable, the mechanism being operative by the user to apply bending force to the support wire to bend the intermediate region and, with it, the microwave antenna relative to the proximal region of the cable.

15. An assembly according to claim 14 and further including a guide tube having a distal region joined to the support wire for positioning the support wire and for holding the support wire while it bends in response to external forces, and wherein the steering wire extends through the guide tube for attachment to the support wire to apply bending force.

16. An assembly according to claim 15
wherein the coaxial cable extends along the exterior of the guide tube.

17. An assembly according to claim 14
and further including solder joining the support wire directly to the intermediate region of the coaxial cable.

18. An assembly according to claim 14
and further including material wrapped about the center support wire and the intermediate cable region joining the support wire directly to the intermediate region of the coaxial cable.

19. An assembly according to claim 18
wherein the material includes shrink fit tubing.

20. An assembly according to claim 14
and further including the material wrapped around the steering wire to hold the steering wire against the center support wire against the support wire.

21. A steerable coaxial cable assembly for a catheter comprising
a coaxial cable having a proximal region for connection to a source of energy and a distal region connected to an energy transmitting element carried on said distal region, the coaxial cable having an intermediate region between the distal and proximal regions that has a greater degree of flexibility than the proximal region, and
a support wire connected directly to the intermediate region of the coaxial cable to bend the intermediate cable region in response to bending force applied to the support wire, a steering wire attached to the support wire and extending from there to a mechanism located at the proximal region of the coaxial cable, the mechanism being operative by the user to apply bending force to the support wire to bend the intermediate region and, with it, the distal region of the coaxial cable relative to its proximal region.

22. An assembly according to claim 21
and further including a guide tube having a distal region joined to the support wire for positioning the support wire and for holding the support wire while it bends in response to external forces, and
wherein the steering wire extends through the guide tube for attachment to the support wire to apply bending force.

23. An assembly according to claim 22
wherein the coaxial cable extends along the exterior of the guide tube.

24. An assembly according to claim 21
and further including solder joining the support wire directly to the intermediate region of the coaxial cable.

25. An assembly according to claim 21
and further including material wrapped about the center support wire and the intermediate cable region joining the support wire directly to the intermediate region of the coaxial cable.

26. An assembly according to claim 25
wherein the material includes shrink fit tubing.

27. An assembly according to claim 21
and further including material wrapped around the steering wire to hold the steering wire against the support wire.

28. An assembly according to claim 21
wherein the intermediate region includes an electroplastic conforming coating.

29. A catheter comprising
guide tube having a distal end,
a center support wire that is bendable in response to external forces and having a proximal end that is joined to the guide tube for holding the center support wire while it bends in response to external forces,
a steering wire attached to a distal end of the center support wire for applying a bending force,
a coaxial cable having a first region that extends along the guide tube, a second region that extends beyond the guide tube, and an intermediate region that extends beyond the second region and includes an energy transmitting element, the second region having a greater degree of flexibility than the first region, and
means connecting the distal end of the center support wire directly to the second region for bonding the second region in response to the bending force applied by the steering wire to the center support wire.

30. An assembly according 29
wherein the means for connecting the center support wire directly to the second region includes means wrapped around the center support wire and the intermediate region.

31. An assembly according to claim 30
wherein the wrapped means includes shrink fit tubing.

32. An assembly according to claim 29
wherein the attachment between the steering wire and the center support wire includes means wrapped around the steering wire to hold the steering wire against the center support wire.

33. An assembly according to claim 29
wherein the intermediate region includes an electroplastic conforming coating.

* * * * *